(12) United States Patent
Carmi

(10) Patent No.: US 12,347,001 B2
(45) Date of Patent: Jul. 1, 2025

(54) SYSTEM AND METHOD FOR PET-CT IMAGE ARTIFACT EVALUATION AND CORRECTION

(71) Applicant: GE Precision Healthcare LLC, Wauwatosa, WI (US)

(72) Inventor: Raz Carmi, Haifa (IL)

(73) Assignee: GE Precision Healthcare LLC, Wauwatosa, WI (US)

( * ) Notice: Subject to any disclaimer, the term of this patent is extended or adjusted under 35 U.S.C. 154(b) by 509 days.

(21) Appl. No.: 17/882,784

(22) Filed: Aug. 8, 2022

(65) Prior Publication Data

US 2024/0046535 A1 Feb. 8, 2024

(51) Int. Cl.
*G06T 11/00* (2006.01)
*A61B 6/00* (2024.01)
*G06T 7/33* (2017.01)

(52) U.S. Cl.
CPC .......... *G06T 11/008* (2013.01); *A61B 6/5235* (2013.01); *A61B 6/5264* (2013.01);
(Continued)

(58) Field of Classification Search
CPC ......... G06T 11/008; G06T 2207/10081; G06T 2207/10104; G06T 2207/10108;
(Continued)

(56) References Cited

U.S. PATENT DOCUMENTS

2006/0285737 A1* 12/2006 Hamill ...................... G06T 5/70
382/131

2015/0117733 A1* 4/2015 Manjeshwar ......... G06T 11/003
382/131
(Continued)

OTHER PUBLICATIONS

McQuaid, Sarah. Characterisation and correction of respiratory-motion artefacts in cardiac PET-CT. Diss. UCL (University College London), 2009. (Year: 2009).*
(Continued)

*Primary Examiner* — Geoffrey E Summers
(74) *Attorney, Agent, or Firm* — Fletcher Yoder, P.C.

(57) ABSTRACT

A method includes obtaining emission-tomography functional image data and a corresponding reconstructed anatomical image volume including at least one organ having natural motion; pre-determining a dedicated model for spatial mismatch correction of the at least one organ; performing initial image reconstruction of the emission-tomography functional image data to generate a reconstructed emission-tomography functional image volume utilizing attenuation correction based on the corresponding reconstructed anatomical image volume; and identifying relevant anatomical regions, within both image volumes, where functional image quality may be affected by the natural motion of the at least one organ. The method includes identifying and evaluating potential attenuation-correction image artifacts in the reconstructed emission-tomography functional image volume; estimating model parameters based on confirmed attenuation-correction image artifacts; correcting the corresponding reconstructed anatomical image volume to generate a corrected anatomical image volume; and reconstructing the emission-tomography functional image data utilizing attenuation correction based on the corrected anatomical image volume.

20 Claims, 9 Drawing Sheets

(52) U.S. Cl.
CPC .... *G06T 7/344* (2017.01); *G06T 2207/10081* (2013.01); *G06T 2207/10104* (2013.01); *G06T 2207/10108* (2013.01); *G06T 2207/20084* (2013.01)

(58) Field of Classification Search
CPC ....... G06T 7/30–38; G06T 2207/20081; G06T 2207/20084; A61B 6/5258; A61B 6/5264; A61B 6/03; A61B 6/032; A61B 6/037; A61B 6/5235
See application file for complete search history.

(56) References Cited

U.S. PATENT DOCUMENTS

| | | | | |
|---|---|---|---|---|
| 2019/0147588 | A1* | 5/2019 | Rowley Grant | G06T 7/0012 382/131 |
| 2021/0012546 | A1* | 1/2021 | Wieczorek | G06T 11/008 |
| 2023/0260141 | A1* | 8/2023 | Schaefferkoetter | A61B 6/463 382/131 |

OTHER PUBLICATIONS

Lee, Jae Sung. "A review of deep-learning-based approaches for attenuation correction in positron emission tomography." IEEE Transactions on Radiation and Plasma Medical Sciences 5.2 (2020): 160-184. (Year: 2020).*
Conti, "Why is TOF PET Reconstruction a More Robust Method in the Presence of Inconsistent Data?", Physics in Medicine and Biology, Nov. 30, 2010, 16 pgs, IOP Publishing, United Kingdom.
Mehranian et al., "Impact of Time-of-Flight PET on Quantification Errors in MR Imaging-Based Attenuation Correction," Apr. 2015, pp. 635-641, vol. 56, No. 4, The Journal of Nuclear Medicine.

* cited by examiner

SYSTEM AND METHOD FOR PET-CT IMAGE ARTIFACT EVALUATION AND CORRECTION

BACKGROUND

The subject matter disclosed herein relates to medical imaging and, more particularly, to medical image artifact correction.

Non-invasive imaging technologies allow images of the internal structures or features of a patient/object to be obtained without performing an invasive procedure on the patient/object. In particular, such non-invasive imaging technologies rely on various physical principles (such as the differential transmission of X-rays through a target volume, the reflection of acoustic waves within the volume, the paramagnetic properties of different tissues and materials within the volume, the breakdown of targeted radionuclides within the body, and so forth) to acquire data and to construct images or otherwise represent the observed internal features of the patient/object.

In functional medical imaging modalities such as positron emission tomography (PET) and single photon emission computed tomography (SPECT), attenuation correction is an important part of the image reconstruction process. Typically, the data for an attenuation correction algorithm is generated from an associated anatomical image scan with computed tomography (CT) or magnetic resonance imaging (MM). For achieving high quality functional images, the spatial matching or registration between the two modalities needs to be accurate. Common sources of image misregistration are sporadic patient movement and natural respiratory motion or cardiac organ motion. Although it would be always beneficial to achieve functional and anatomical image data acquired at the same patient motion phase, this is usually difficult to accomplish with the typical clinical protocol considerations. Therefore, attempts have been made to algorithmically correct this problem within an image reconstruction framework.

Attenuation-correction mismatch image artifacts can affect the accuracy and reliability of clinical diagnostics since radiotracer uptake in lesions or other structured tissues may appear significantly too low or too high relative to the true values. For example, lesions in the upper liver region or lesions in the lower lung areas may significantly be affected by respiratory motion leading to functional-anatomical mismatch. In cardiac imaging, the left ventricle imaged uptake may be affected by the myocardium expansion and contraction cycle. A related common problem is that imaged regions of the lower lung have strong activity value suppression which may cause the physician to miss the true clinical findings.

Several different approaches have been attempted in trying to mitigate the described artifact problem. In one known approach, in PET and SPECT, the reviewed functional images are typically the average along time of the acquired data during natural organ motion, or they are the result of a selected reconstructed phase (i.e., "freeze" state) from a gated acquisition (instrumental-based or data-driven). The corresponding anatomical images, like from CT, are typically acquired in an asynchronized breath-hold scan, or in an arbitrary short time frame from a natural-breathing scan. It is possible to select a specific reconstructed PET phase with probable best registration to the CT images. However, in this approach, the PET image quality may be significantly degraded, and the optimal registration to the CT is still not guaranteed. Additionally, known approaches of 3D image-based PET-CT registration can help as well, but only if there is sufficient structural similarity between the relevant functional and anatomical image structures. Unfortunately, such similarity is not always guaranteed, and particularly large structural differences may exist in situations with severe artifact. Further, some other combinations and variations of these approaches were investigated as well. In any practical chosen solution, the overall computational time should also be an important consideration.

In addition, the described artifact problem may be worse (i.e., attenuation mismatch artifacts are stronger) in PET systems lacking time-of-flight (TOF) capabilities. In particular, these artifacts may appear in total body, non-TOF PET systems with wide coincidence acceptance angle, where the projection rays may frequently pass particularly high attenuation paths in the patient body.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a computer-implemented method for automatic artifact evaluation and correction in medical imaging data is provided. The method includes obtaining, via a processor, emission-tomography functional image data and a corresponding reconstructed anatomical image volume of a subject, the emission-tomography functional image data and the corresponding reconstructed anatomical image volume including at least one organ having natural motion. The method also includes pre-determining, via the processor, a dedicated model for spatial mismatch correction of the at least one organ having natural motion. The method further includes performing, via the processor, initial image reconstruction of the emission-tomography functional image data to generate a reconstructed emission-tomography functional image volume utilizing attenuation correction based on the corresponding reconstructed anatomical image volume. The method even further includes identifying, via the processor, relevant anatomical regions, within the reconstructed emission-tomography functional image volume and the corresponding reconstructed anatomical image volume, where functional image quality may be affected by the natural motion of the at least one organ. The method still further includes identifying and evaluating, via the processor, potential attenuation-correction image artifacts in the reconstructed emission-tomography functional image volume that are related to functional-anatomical spatial mismatch. The method yet further includes estimating, via the processor, model parameters based on confirmed attenuation-correction image artifacts, wherein the model parameters represent the functional-anatomical spatial mismatch. The method further includes correcting, via the processor, the corresponding reconstructed anatomical image volume utilizing both the dedicated model and the model parameters to generate a corrected anatomical image volume. The method still further includes reconstructing, via the processor, the emission-tomography functional image data utilizing attenuation correction based on the corrected anatomical image volume to generate a corrected emission-tomography functional image volume.

In another embodiment, a system for automatic artifact evaluation and correction in medical imaging data is provided. The system includes a memory encoding processor-executable routines. The system also includes a processor configured to access the memory and to execute the processor-executable routines, wherein the routines, when executed by the processor, cause the processor to perform actions. The actions include obtaining emission-tomography functional image data and a corresponding reconstructed anatomical image volume of a subject, the emission-tomography functional image data and the corresponding reconstructed anatomical image volume including at least one organ having natural motion. The actions also include predetermining a dedicated model for spatial mismatch correction of the at least one organ having natural motion. The actions further include performing initial image reconstruction of the emission-tomography functional image data to generate a reconstructed emission-tomography functional image volume utilizing attenuation correction based on the corresponding reconstructed anatomical image volume. The actions even further include identifying relevant anatomical regions, within the reconstructed emission-tomography functional image volume and the corresponding reconstructed anatomical image volume, where functional image quality may be affected by the natural motion of the at least one organ. The actions still further include identifying and evaluating potential attenuation-correction image artifacts in the reconstructed emission-tomography functional image volume that are related to functional-anatomical spatial mismatch. The actions yet further include estimating model parameters based on confirmed attenuation-correction image artifacts, wherein the model parameters represent the functional-anatomical spatial mismatch. The actions further include correcting the corresponding reconstructed anatomical image volume utilizing both the dedicated model and the model parameters to generate a corrected anatomical image volume. The actions still further include reconstructing the emission-tomography functional image data utilizing attenuation correction based on the corrected anatomical image volume to generate a corrected emission-tomography functional image volume.

In a further embodiment, a non-transitory computer-readable medium is provided. The computer-readable medium includes processor-executable code that when executed by a processor, causes the processor to perform actions. The actions include obtaining emission-tomography functional image data and a corresponding reconstructed anatomical image volume of a subject, the emission-tomography functional image data and the corresponding reconstructed anatomical image volume including at least one organ having natural motion. The actions also include predetermining a dedicated model for spatial mismatch correction of the at least one organ having natural motion. The actions further include performing initial image reconstruction of the emission-tomography functional image data to generate a reconstructed emission-tomography functional image volume utilizing attenuation correction based on the corresponding reconstructed anatomical image volume. The actions even further include identifying relevant anatomical regions, within the reconstructed emission-tomography functional image volume and the corresponding reconstructed anatomical image volume, where functional image quality may be affected by the natural motion of the at least one organ. The actions still further include identifying and evaluating potential attenuation-correction image artifacts in the reconstructed emission-tomography functional image volume that are related to functional-anatomical spatial mismatch. The actions yet further include estimating model parameters based on confirmed attenuation-correction image artifacts, wherein the model parameters represent the functional-anatomical spatial mismatch. The actions further include correcting the corresponding reconstructed anatomical image volume utilizing both the dedicated model and the model parameters to generate a corrected anatomical image volume. The actions still further include reconstructing the emission-tomography functional image data utilizing attenuation correction based on the corrected anatomical image volume to generate a corrected emission-tomography functional image volume.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
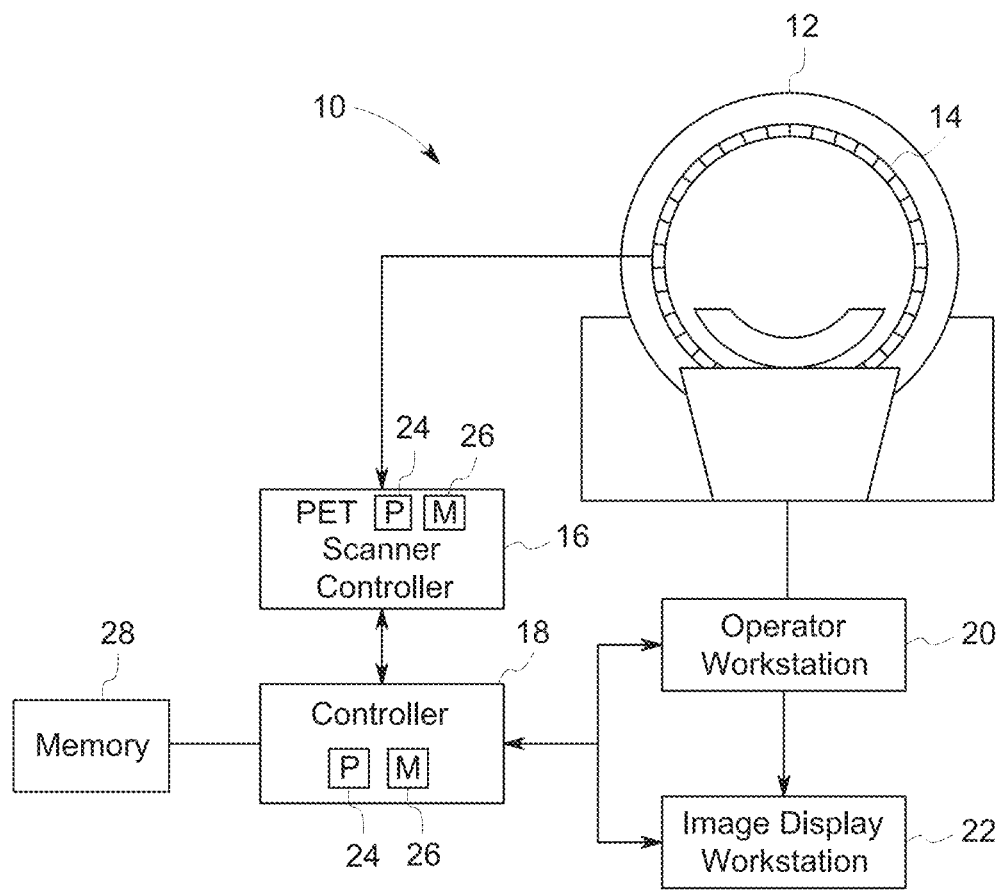
FIG. 1 is a diagrammatical representation of an embodiment of a PET imaging system, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As utilized herein, "functional medical imaging" relates to revealing physiological activities within a certain tissue or organ by employing medical image modalities (e.g., PET, SPECT, CT perfusion imaging, functional MM) that often utilize tracers or probes to reflect spatial distribution of them within the body. As utilized herein, "anatomical medical imaging" or "structural medical imaging" relates to the visualization and analysis of anatomical properties of a certain tissue or organ utilizing certain medical image modalities (e.g., CT, structural Mill, diffused-based MRI).

Machine learning techniques, whether deep learning networks or other experiential/observational learning system, can be used to locate an object in an image, understand speech and convert speech into text, and improve the relevance of search engine results, for example. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

Throughout the specification and claims, the following terms take the meanings explicitly associated herein, unless the context clearly dictates otherwise. The term "deep learning" is a machine learning technique that utilizes multiple data processing layers to recognize various structures in data sets and classify the data sets with high accuracy. A deep learning network can be a training network (e.g., a training network model or device) that learns patterns based on a plurality of inputs and outputs. A deep learning network can be a deployed network (e.g., a deployed network model or device) that is generated from the training network and provides an output in response to an input.

The present disclosure provides systems and methods for automatic artifact evaluation and correction in medical imaging data. In particular, the described systems and methods take a different approach from those described above to address attenuation-correction mismatch image artifacts (e.g., due to PET-CT respiratory mismatch). The disclosed systems and methods utilize a dedicated algorithm (e.g., automatic artifact evaluation and correction algorithm) to evaluate the originally reconstructed PET image artifacts. The algorithm is based on accurately identifying the relevant anatomical regions which may be susceptible to artifacts, and some other relevant organs or regions. Then, key characteristics of the morphological structures and intensities of the artifacts are calculated based on the PET image values (e.g., for use with a modeled CT image deformation based on estimated respiratory motion pattern). In certain embodiments, this step can be assisted by machine-learning or deep-learning techniques. From this evaluation, the spatial range of either "missing" or "over-presence of" attenuating tissues is estimated. The deformation model of the CT image volume is based on the knowledge that the mismatch is caused by specific natural organ motion, typically periodic. Therefore, it is possible to estimate the structural changes of the relevant organs and their vicinity on different phases along the motion cycle, if main key parameters representing the difference relative to the original imaged phase are known. For example, the respiratory motion in the lower lung region is caused by the diaphragm motion, which mainly causes the liver and spleen to stretch up or down against the adjacent volume and tissues of the lungs. The diaphragm itself is a very thin muscle tissue. This expansion or contraction is typically within predicted limits and morphological constraints. In cardiac motion cycle, it is also possible to estimate the expanded or contracted heart and myocardium shapes along the cycle, if the average phase position along that cycle is known. The derived few key parameters from the image artifact evaluation enables estimating the motion phase along the organ motion cycle, and enables use of the deformation model to modify the CT image volume accordingly. The modified CT is used to reconstruct corrected PET images with more accurate attenuation correction. The goal of the CT deformation process is to achieve an artificial anatomical volume which is much closer to the underlying anatomy positions that correspond to the PET image volume than what the original CT volume provides (even if the artificially deformed CT volume is not fully accurate by itself). The modified CT images may typically be used only for the attenuation correction in the reconstruction and not directly for clinical review and diagnostics.

The disclosed systems and methods provide an approach that can be utilized in situations where severe artifacts exist and any spatial registration algorithms between the PET and CT images cannot provide the required result. In addition, the disclosed systems and methods provide an approach that is particularly suited for large axial coverage non-TOF PET systems (e.g., total body PET systems). The disclosed embodiments can be applied to correct similar artifacts in cardiac PET-CT and other multi-modalities (e.g., SPECT-CT and PET-MM).

With the foregoing in mind and turning now to the drawings, FIG. 1 depicts a PET or SPECT system 10 operating in accordance with certain aspects of the present disclosure. The PET or SPECT imaging system of FIG. 1 may be utilized with a dual-modality imaging system such as a PET-CT imaging system described in FIG. 2 or a PET-MRI imaging system described in FIG. 3.

Returning now to FIG. 1, the depicted PET or SPECT system 10 includes a detector 12 (or detector array). The detector 12 of the PET or SPECT system 10 typically includes a number of detector modules or detector assemblies (generally designated by reference numeral 14) arranged in one or more rings, as depicted in FIG. 1, each detector assembly 14 includes multiple detector units (e.g., 3 to 5 detector units or more). The depicted PET or SPECT system 10 also includes a PET scanner controller 16, a controller 18, an operator workstation 20, and an image display workstation 22 (e.g., for displaying an image). In certain embodiments, the PET scanner controller 16, controller 18, operator workstation 20, and image display workstation 22 may be combined into a single unit or device or fewer units or devices.

The PET scanner controller 16, which is coupled to the detector 12, may be coupled to the controller 18 to enable the controller 18 to control operation of the PET scanner controller 16. Alternatively, the PET scanner controller 16 may be coupled to the operator workstation 20 which controls the operation of the PET scanner controller 16. In operation, the controller 18 and/or the workstation 20 controls the real-time operation of the PET system or SPECT system 10. In certain embodiments the controller 18 and/or the workstation 20 may control the real-time operation of another imaging modality (e.g., the CT imaging system in FIG. 2) to enable the simultaneous and/or separate acquisition of image data from the different imaging modalities. One or more of the PET scanner controller 16, the controller 18, and/or the operation workstation 20 may include a processor 24 and/or memory 26. In certain embodiments, the PET or SPECT system 10 may include a separate memory 28. The detector 12, PET scanner controller 16, the controller 18, and/or the operation workstation 20 may include detector acquisition circuitry for acquiring image data from the detector 12, image reconstruction and processing circuitry for image processing, and/or circuitry for regulating the temperature of the detector units of the detector assemblies 14 (e.g., independently regulating the temperature of each detector assembly 14). The circuitry may include specially programmed hardware, memory, and/or processors.

The processor 24 may include multiple microprocessors, one or more "general-purpose" microprocessors, one or more special-purpose microprocessors, and/or one or more application specific integrated circuits (ASICS), system-on-chip (SoC) device, or some other processor configuration. For example, the processor 24 may include one or more reduced instruction set (RISC) processors or complex instruction set (CISC) processors. The processor 24 may execute instructions to carry out the operation of the PET or SPECT system 10. These instructions may be encoded in programs or code stored in a tangible non-transitory computer-readable medium (e.g., an optical disc, solid state device, chip, firmware, etc.) such as the memory 26, 28. In certain embodiments, the memory 26 may be wholly or partially removable from the controller 16, 18.

By way of example, PET imaging is primarily used to measure metabolic activities that occur in tissues and organs and, in particular, to localize aberrant metabolic activity. In PET imaging, the patient is typically injected with a solution that contains a radioactive tracer. The solution is distributed and absorbed throughout the body in different degrees, depending on the tracer employed and the functioning of the organs and tissues. For instance, tumors typically process more glucose than a healthy tissue of the same type. Therefore, a glucose solution containing a radioactive tracer may be disproportionately metabolized by a tumor, allowing the tumor to be located and visualized by the radioactive emissions. In particular, the radioactive tracer emits positrons that interact with and annihilate complementary electrons to generate pairs of gamma rays. In each annihilation reaction, two gamma rays traveling in opposite directions are emitted. In a PET imaging system 10, the pair of gamma rays are detected by the detector array 12 configured to ascertain that two gamma rays detected sufficiently close in time are generated by the same annihilation reaction. Due to the nature of the annihilation reaction, the detection of such a pair of gamma rays may be used to determine the line of response along which the gamma rays traveled before impacting the detector, allowing localization of the annihilation event to that line. By detecting a number of such gamma ray pairs, and calculating the corresponding lines traveled by these pairs, the concentration of the radioactive tracer in different parts of the body may be estimated and a tumor, thereby, may be detected. Therefore, accurate detection and localization of the gamma rays forms a fundamental and foremost objective of the PET system 10.

Figure 2:
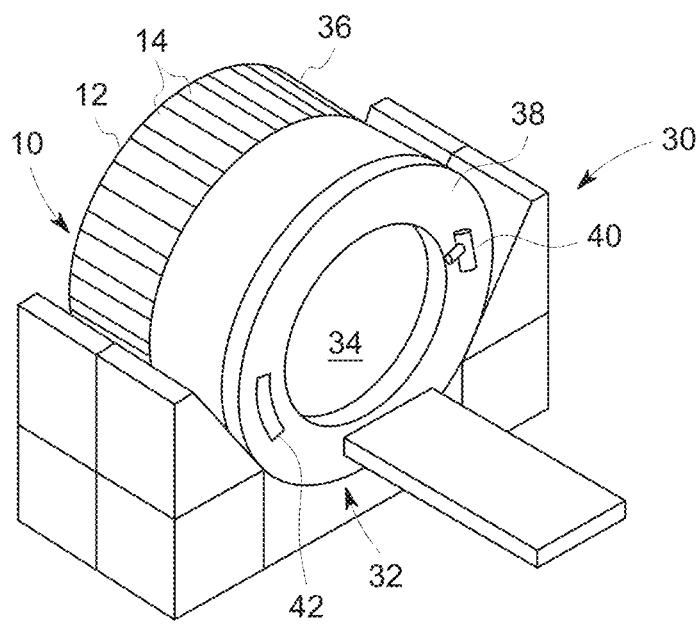
FIG. 2 is a perspective view of a PET-CT imaging system having the PET imaging system of FIG. 1, in accordance with aspects of the present disclosure.

As mentioned above, the PET or SPECT system 10 may be incorporated into a dual-modality imaging system such as the PET-CT imaging system 30 in FIG. 2. Referring now to FIG. 2, the PET-CT imaging system 30 includes the PET system 10 and a CT system 32 positioned in fixed relationship to one another. The PET system 10 and CT system 32 are aligned to allow for translation of a patient (not shown) therethrough. In use, a patient is positioned within a bore 34 of the PET-CT imaging system 30 to image a region of interest of the patient as is known in the art.

The PET system 10 includes a gantry 36 that is configured to support a full ring annular detector array 12 thereon (e.g., including the plurality of detector assemblies 14 in FIG. 1). The detector array 12 is positioned around the central opening/bore 34 and can be controlled to perform a normal "emission scan" in which positron annihilation events are counted. To this end, the detectors 14 forming array 12 generally generate intensity output signals corresponding to each annihilation photon.

The CT system 32 includes a rotatable gantry 38 having an X-ray source 40 thereon that projects a beam of X-rays toward a detector assembly 42 on the opposite side of the gantry 38. The detector assembly 42 senses the projected X-rays that pass through a patient and measures the intensity of an impinging X-ray beam and hence the attenuated beam as it passes through the patient. During a scan to acquire X-ray projection data, gantry 38 and the components mounted thereon rotate about a center of rotation. In certain embodiments, the CT system 32 may be controlled by the controller 18 and/or operator workstation 20 described in FIG. 2. In certain embodiments, the PET system 10 and the CT system 32 may share a single gantry. Image data may be acquired simultaneously and/or separately with the PET system 10 and the CT system 32.

Figure 3:
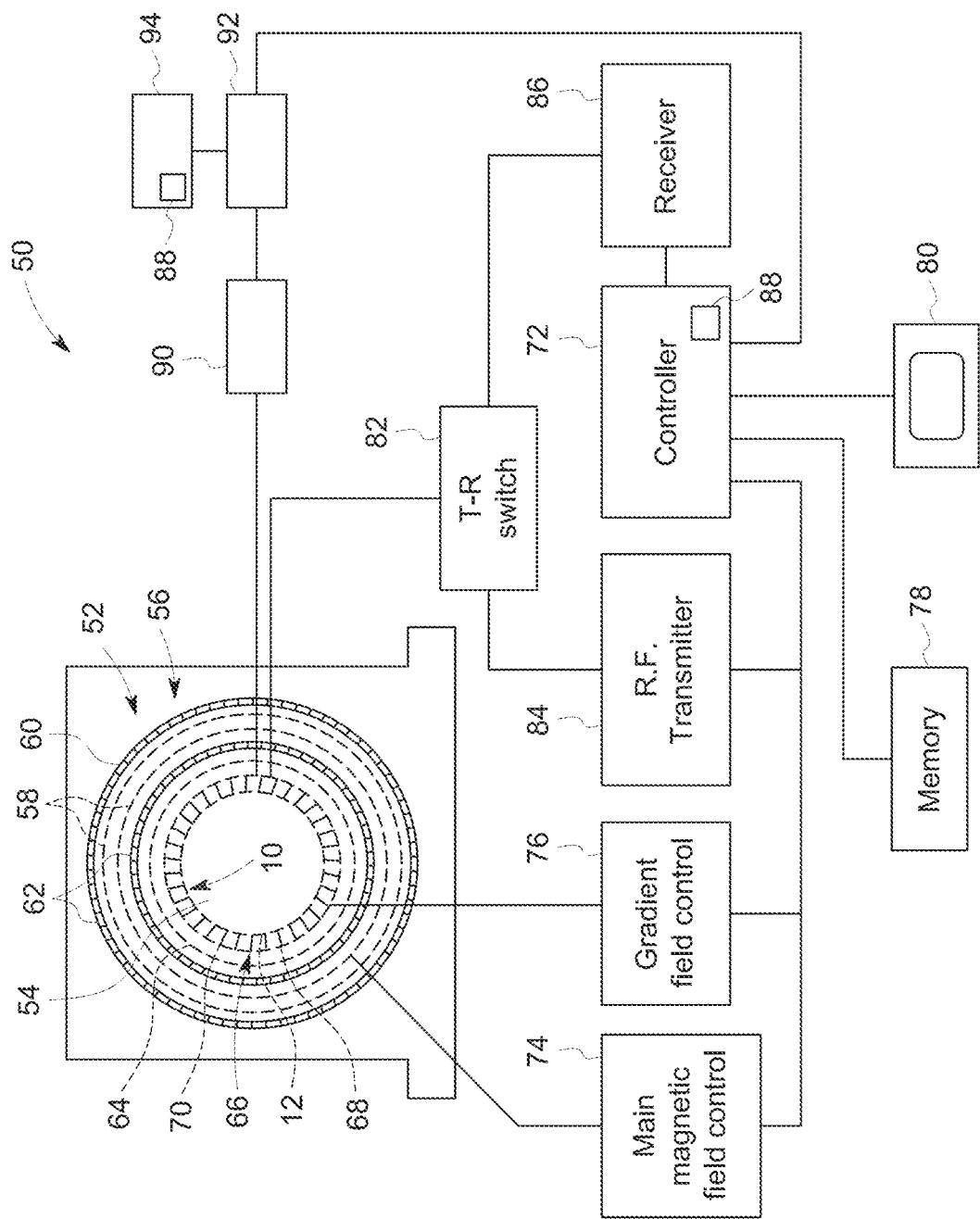
FIG. 3 is a perspective view of a PET-MRI imaging system having the PET imaging system of FIG. 1, in accordance with aspects of the present disclosure.

As mentioned above, the PET or SPECT system 10 may be incorporated into a dual-modality imaging system such as the PET-MM imaging system 50 in FIG. 3. Referring now to FIG. 3, the PET-MRI imaging system 50 includes the PET system 10 and a MM system 52 positioned in fixed relationship to one another. The PET system 10 and MRI system 52 are aligned to allow for translation of a patient (not shown) therethrough. In use, a patient is positioned within a bore 54 of the PET-CT imaging system 50 to image a region of interest of the patient as is known in the art. Image data may be acquired simultaneously and/or separately with the PET system 10 and the MRI system 52.

The PET-MRI imaging system 50 that includes a superconducting magnet assembly 56 that includes a superconducting magnet 58. The superconducting magnet 58 is formed from a plurality of magnetic coils supported on a magnet coil support or coil former. In one embodiment, the superconducting magnet assembly 56 may also include a thermal shield 60. A vessel 62 (also referred to as a cryostat) surrounds the superconducting magnet 58, and the thermal shield 60 surrounds the vessel 62. The vessel 62 is typically filled with liquid helium to cool the coils of the superconducting magnet 58. A thermal insulation (not shown) may be provided surrounding the outer surface of the vessel 62. The imaging system 50 also includes a main gradient coil 64, and the RF coil assembly 66 that is mounted radially inwardly from the main gradient coil 64. As described above, a radio frequency (RF) coil assembly 66 includes the PET detector assembly 12, an RF transmit coil 68 and the RF shield 70. More specifically, the RF coil assembly 66 includes a coil support structure that is used to mount the PET detector assembly 12, the RF transmit coil 68, and the RF shield 70.

In operation, the RF coil assembly 66 enables the imaging system 50 to perform both MM and PET imaging concurrently because both the RF transmit coil 68 and the PET detector assembly 12 are placed around a patient at the center of the bore of the imaging system 50. Moreover, the PET detector assembly 12 is shielded from the RF transmit coil 68 using the RF shield 70 that is disposed between the RF transmit coil 68 and the PET detector assembly 12. Mounting the PET detector assembly 12, the RF transmit coil 68 and the RF shield 70 on the coil support structure enables the RF coil assembly 66 to be fabricated to have an outside diameter that enables the RF coil assembly 66 to be mounted inside the gradient coil 64. Moreover, mounting the PET detector assembly 12, the RF transmit coil 68 and the RF shield 70 on the coil support structure enables the RF coil assembly 66 to have a relatively large inside diameter to enable the imaging system 50 to image larger patients.

The imaging system 50 also generally includes a controller 72, a main magnetic field control 74, a gradient field control 76, a memory 78, a display device 80, a transmit-receive (T-R) switch 82, an RF transmitter 84, and a receiver 86.

In operation, a body of an object, such as a patient (not shown), or a phantom to be imaged, is placed in the bore 54 on a suitable support, for example, a motorized table (not shown) or the cradle described above. The superconducting magnet 58 produces a uniform and static main magnetic field Bo across the bore 54. The strength of the electromagnetic field in the bore 54 and correspondingly in the patient, is controlled by the controller 72 via the main magnetic field control 74, which also controls a supply of energizing current to the superconducting magnet 58.

The main gradient coil 64, which may include one or more gradient coil elements, is provided so that a magnetic gradient can be imposed on the magnetic field BO in the bore 54 in any one or more of three orthogonal directions x, y, and z. The main gradient coil 64 is energized by the gradient field control 76 and is also controlled by the controller 72.

The RF coil assembly 66 is arranged to transmit magnetic pulses and/or optionally simultaneously detect MR signals from the patient, if receive coil elements are also provided. The RF coil assembly 66 may be selectably interconnected to one of the RF transmitter 84 or receiver 86, respectively, by the T-R switch 82. The RF transmitter 84 and T-R switch 82 are controlled by the controller 72 such that RF field pulses or signals are generated by the RF transmitter 84 and selectively applied to the patient for excitation of magnetic resonance in the patient.

Following application of the RF pulses, the T-R switch 82 is again actuated to decouple the RF coil assembly 66 from the RF transmitter 84. The detected MR signals are in turn communicated to the controller 72. The controller 72 includes a processor 88 that controls the processing of the MR signals to produce signals representative of an image of the patient. The processed signals representative of the image are also transmitted to the display device 80 to provide a visual display of the image. Specifically, the MR signals fill or form a k-space that is Fourier transformed to obtain a viewable image which may be viewed on the display device 80.

The imaging system 50 also controls the operation of PET imaging. Accordingly, in various embodiments, the imaging system 50 may also include a coincidence processor 90 that is coupled between the detector 12 and a PET scanner controller 92. The PET scanner controller 92 may be coupled to the controller 72 to enable the controller 72 to control the operation of the PET scanner controller 92. Optionally, the PET scanner controller 92 may be coupled to a workstation 94 which controls the operation of the PET scanner controller 92. In operation, the exemplary embodiment, the controller 72 and/or the workstation 94 controls real-time operation of the PET imaging portion of the imaging system 50.

More specifically, in operation, the signals output from the PET detector assembly 12 are input to the coincidence processor 90. In various embodiments, the coincidence processor 90 assembles information regarding each valid coincidence event into an event data packet that indicates when the event took place and the position of a detector that detected the event. The valid events may then be conveyed to the controller 92 and utilized to reconstruct an image. Moreover, it should be realized that images acquired from the MR imaging portion may be overlaid onto images acquired from the PET imaging portion. The controller 72 and/or the workstation 94 may a central processing unit (CPU) or computer 88 to operate various portions of the imaging system 50. As used herein, the term "computer" may include any processor-based or microprocessor-based system configured to execute the methods described herein. Accordingly, the controller 72 and/or the workstation 94 may transmit and/or receive information from the PET detector assembly 12 to both control the operation of the PET detector assembly 12 and to receive information from the PET detector assembly 12.

The various embodiments and/or components, for example, the modules, or components and controllers therein, such as of the imaging system 50, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the disclosed subject matter. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Figure 4:
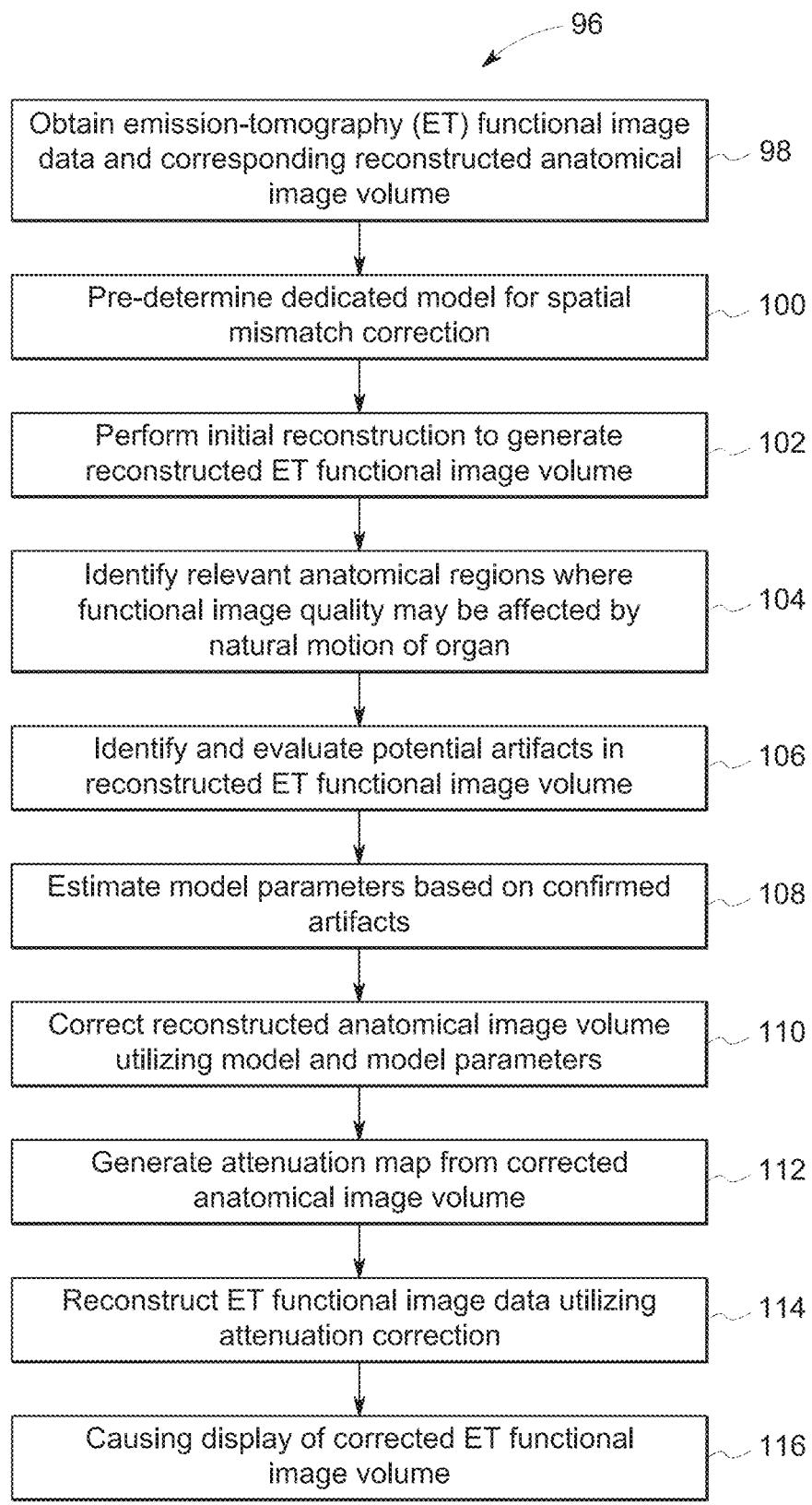
FIG. 4 is a flowchart of a method for automatic artifact evaluation and correction in medical imaging data, in accordance with aspects of the present disclosure.

FIG. 4 is a flowchart of a method 96 (e.g., automatic artifact evaluation and correction algorithm) for automatic artifact evaluation and correction in medical imaging data. One or more steps of the method 96 may be performed by processing circuitry of the imaging systems discussed above or processing circuitry of a remote computing device having processing circuitry and memory circuitry. One or more of the steps of the method 96 may be performed simultaneously or in a different order from the order depicted in FIG. 4.

The method 96 includes obtaining emission-tomography functional image data and a corresponding reconstructed anatomical image volume of a subject (e.g., patient), the emission-tomography functional image data and the corresponding reconstructed anatomical image volume including at least one organ having natural motion (block 98). In certain embodiments, this imaging data may be acquired for multiple organs having natural motion. For example, the emission-tomography functional image data may be acquired PET image data of the subject with may be reconstructed with controlled parameters and assisting information (e.g., different attenuation maps). The corresponding reconstructed anatomical image volume may be a corresponding CT image volume of the same patient. As an example, the PET and CT image data may include lower regions of the lungs (or in a different example, the heart). These regions or organs have natural motion during the PET scan (e.g., which typically lasts a few minutes) or during the "freeze" state phase (e.g., from a gated acquisition) within the organ motion cycle.

The method 96 also includes pre-determining a dedicated model for spatial mismatch correction of the at least one organ having natural motion (block 100). In certain embodiments, different dedicated models for spatial mismatch correction may be pre-determined for different organs having natural motion. The pre-determined model is based on the assumption that if an image volume of the organ vicinity is given in a specific (or arbitrary) cycle phase, just a few parameters (e.g., one or two parameters) are sufficient to predict how the organ vicinity should be seen (at least roughly) on the images on a different cycle phase. For example, one such parameter may represent the mean of the organ edge between two different phases along the cycle. For example, in the lower lung region, the organ edge could be the upper edge of the liver or the spleen. As another example, the organ edge in the heart could be left edge of the left ventricle. The model determines how to artificially transform or modify the organ structures on the images based on the calculated parameters. The estimation or determination of these parameters is explained in greater detail below.

The method 96 further includes performing initial image reconstruction of the emission-tomography functional image data to generate a reconstructed emission-tomography functional image volume utilizing attenuation correction based on the corresponding reconstructed anatomical image volume (block 102). This step is a standard initial reconstruction step.

The method 96 even further include identifying relevant anatomical regions (e.g., in a sub-volume), within the reconstructed emission-tomography functional image volume and the corresponding reconstructed anatomical image volume, where functional image quality may be affected by the natural motion of the at least one organ (block 104). In certain embodiments, relevant anatomical regions may be identified for different organs with natural motion. For example, computer-vision and image processing techniques may be utilized to automatically detect a sub-volume including the lower part of the lungs and the upper parts of the liver and spleen. The sub-volume may be detected on the CT anatomical image volume (based on Hounsfield units (HU)) by first applying a rough lung detection and segmentation algorithm. On the lung mask, the lower edges and the outer circumference of the lungs on this lower region may be automatically identified. In certain embodiments, a whole body (e.g., soft tissue) volumetric segmented mask may be utilized to identify the relevant anatomical region. The identified relevant anatomical region could be a volumetric slab with approximately a few centimeters width in the Z-direction (e.g. axial patient direction) and an ellipse shape in the XY (transverse) direction.

The method 96 still further includes identifying and evaluating potential attenuation-correction image artifacts in the reconstructed emission-tomography functional image volume that are related to functional-anatomical spatial mismatch (block 106). For example, in a determined or identified relevant anatomical region, the algorithm (e.g., automatic artifact evaluation and correction algorithm) may search for voxels with functional image values (e.g., PET image values such as standardized uptake values (SUV)) that are suspected to be too low or too high relative to mean values (e.g., mean PET image values) in adjacent organs and tissues. For the identified voxels with too low or too high of functional image values, characteristics such as the intensities, shapes (e.g., morphology), size, and location of these group of voxels may be evaluated.

The method 96 yet further includes estimating model parameters based on confirmed attenuation-correction image artifacts, wherein the model parameters represent the functional-anatomical spatial mismatch (block 108). For example, the characteristics of the identified voxels may be utilized to determine the few model parameters. Examples of the model parameters that are calculated are determined are a width in Z and curvature change along XY. The model parameters are utilized in determining the required CT deformation. Block 106 and 108 are described in greater detail in FIG. 5.

The method 96 further includes correcting the corresponding reconstructed anatomical image volume utilizing both the dedicated model and the model parameters to generate a corrected anatomical image volume (block 110). For example, a new CT image volume may be generated where the liver, spleen, and their adjacent tissues are expanded toward the lungs, to imitate a situation similar to when the subject exhales part of the air in the lungs. Block 110 is described in greater detail in FIG. 6.

The method 96 even further includes generating an attenuation map from the corrected anatomical image volume (block 112). For example, a new attenuation map may be generated based on the new CT image volume. The method 96 still further includes reconstructing the emission-tomography functional image data utilizing attenuation correction based on the corrected anatomical image volume to generate a corrected emission-tomography functional image volume (block 114). For example, a corrected PET image volume is reconstructed using the original PET data and the new attenuation map.

The method 96 yet further includes causing the display of the corrected emission-tomography functional image volume on a display (e.g., user interface) (block 116). For corrected PET image volume may be visualized together (e.g., fused) with the original diagnostic CT image volume. In certain embodiments, the corrected PET image volume may be visualized together with the deformed CT image volume (e.g., corrected anatomical image volume). Although the deformed CT image volume may be better registered, the diagnostic accuracy of anatomical details may be compromised. Thus, in the latter case, a clear indication should be provided to user to indicate that the CT image is deformed. In certain embodiments, the method 96 may be utilized in conjunction with an attenuation correction quality check (ACQC) user application. In such an application, the corrected PET images can be viewed (e.g., on a user interface) in comparison with the original PET images (e.g., sometimes fused). In addition, the visualized detected image with an indication of the calculated required anatomical shifts. In certain embodiments, the interactive application may enable a user to manually refine these shifts (e.g., as a ±ΔZ) and apply a refined PET image reconstruction.

The method 96 includes a number of advantages. For example, the method 96 does not need list-mode or gated PET reconstruction. Only the standard original reconstruction and final reconstruction are needed with an image processing/analysis algorithm in the middle between the original and final reconstructions. With only two standard reconstructions, the method 96 provides a reasonable overall computational time. In addition, the method 96 is well suited for situations where severe artifacts exits. In particular, situations with strong regional activity suppression where any known spatial registration algorithm between the PET and CT images cannot provide the required result. Further, as noted above, the method 96 may be efficiently integrated with an ACQC user application.

Figure 5:
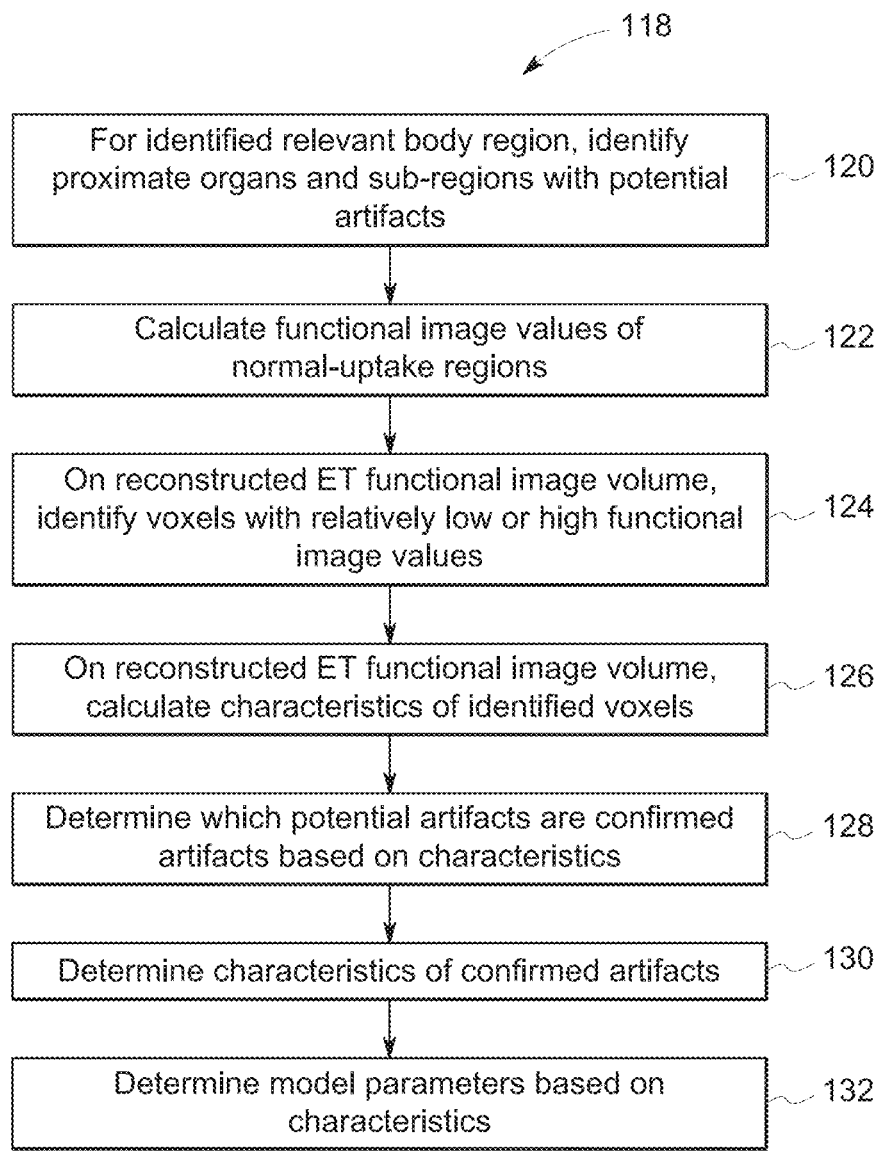
FIG. 5 is a flowchart of a method for detecting and estimating model parameters of attenuation-correction image artifacts, in accordance with aspects of the present disclosure.

FIG. 5 is a flowchart of a method 118 for detecting and estimating model parameters of attenuation-correction image artifacts (e.g., blocks 106 and 108 of the method 96 in FIG. 4). One or more steps of the method 118 may be performed by processing circuitry of the imaging systems discussed above or processing circuitry of a remote computing device having processing circuitry and memory circuitry. One or more of the steps of the method 118 may be performed simultaneously or in a different order from the order depicted in FIG. 5.

The method 118 includes, for each determined or identified relevant anatomical region (e.g., sub-region or sub-volume), proximate organs and specific sub-regions with the potential attenuation-correction image artifacts (block 120). For example, the relevant sub-region for searching for artifacts may be a volumetric slab which is placed on the lower lung region and that includes the upper regions of the liver and the spleen. The proximate organs may be the whole lung volume (e.g., as a voxel mask) and the segmented liver volume (usually a rough segmentation is sufficient).

The method 118 also includes calculating functional image values of normal-uptake regions (e.g., normal relevant to adjacent organ and tissues) in the identified proximate organs (and/or identified sub-regions) (block 122). For example, the calculated functional image values may be the median of PET image values (e.g., SUV) on a voxel mask that includes body soft tissues (e.g., located with the help of the CT HU values of the whole scanned patient). The calculated functional image values may also be the median of the PET image values on the whole lungs. The calculated images may further be the median of the PET image values on the whole liver. In certain embodiments, other statistical functions (e.g., mean) other than the median may be utilized.

The method 118 further includes, on the reconstructed emission-tomography functional image volume, identifying voxels with relatively low functional image values or relatively high functional image values compared to the calculated functional image values of the normal-uptake regions based on pre-determined criteria (block 124). For example, the PET image values in the volumetric slab (e.g., from block 120) may be compared relative to the normal uptake values obtained in block 122. The pre-determined criteria may be logical criteria that includes differences, ratios, and/or parameter thresholds. In certain embodiments, deviation levels may also be calculated and utilized to determine how much is too high and how much is too low.

The method 118 still further includes, on the reconstructed emission-tomography functional image volume, calculating characteristics of any identified voxels with the relatively low functional image values or the relatively high functional image values relative to the identified proximate organs (block 126). The groups of identified voxels create three-dimensional (3D) shapes in the image space. The intensities, shape morphology, sizes, and their spatial locations relative to the adjacent body organs are important for evaluating whether the group of identified voxels are attenuation-correction image artifacts. In addition, statistical characteristics (e.g., histogram analysis, center-of-mass, etc.) of the spatial distribution of the identified voxels may be relevant for the evaluation.

The method 118 yet further includes determining which of the potential attenuation-correction image artifacts are confirmed attenuation-correction image artifacts based on characteristics of the identified voxels (block 128). This determination is based on the information (e.g., identified voxels and characteristics of the identified voxels) from blocks 124 and 126.

The method 118 even further includes determining characteristics of the confirmed attenuation-correction image artifacts relevant for attenuation correction based on the pre-determined criteria (block 130). From the information from blocks 124 and 126, the final characteristics of the actual or confirmed attenuation-correction image artifacts may be determined utilizing the pre-determined criteria mentioned above.

The method 118 further includes estimating or determining the model parameters based on confirmed attenuation-correction image artifacts, wherein the model parameters represent the functional-anatomical spatial mismatch (block 132). This is equivalent to the block 108 of the method 96 in FIG. 4. Based on the final artifact characteristics, key parameters (typically, only a few parameters) are determined to control the subsequent CT image volume deformation (e.g., used to correct for the functional-anatomical spatial mismatch). For example, the parameters may include the expansion or contraction width and/or curvatures of conditional dilation (or conditional contraction) of a morphological process.

Figure 6:
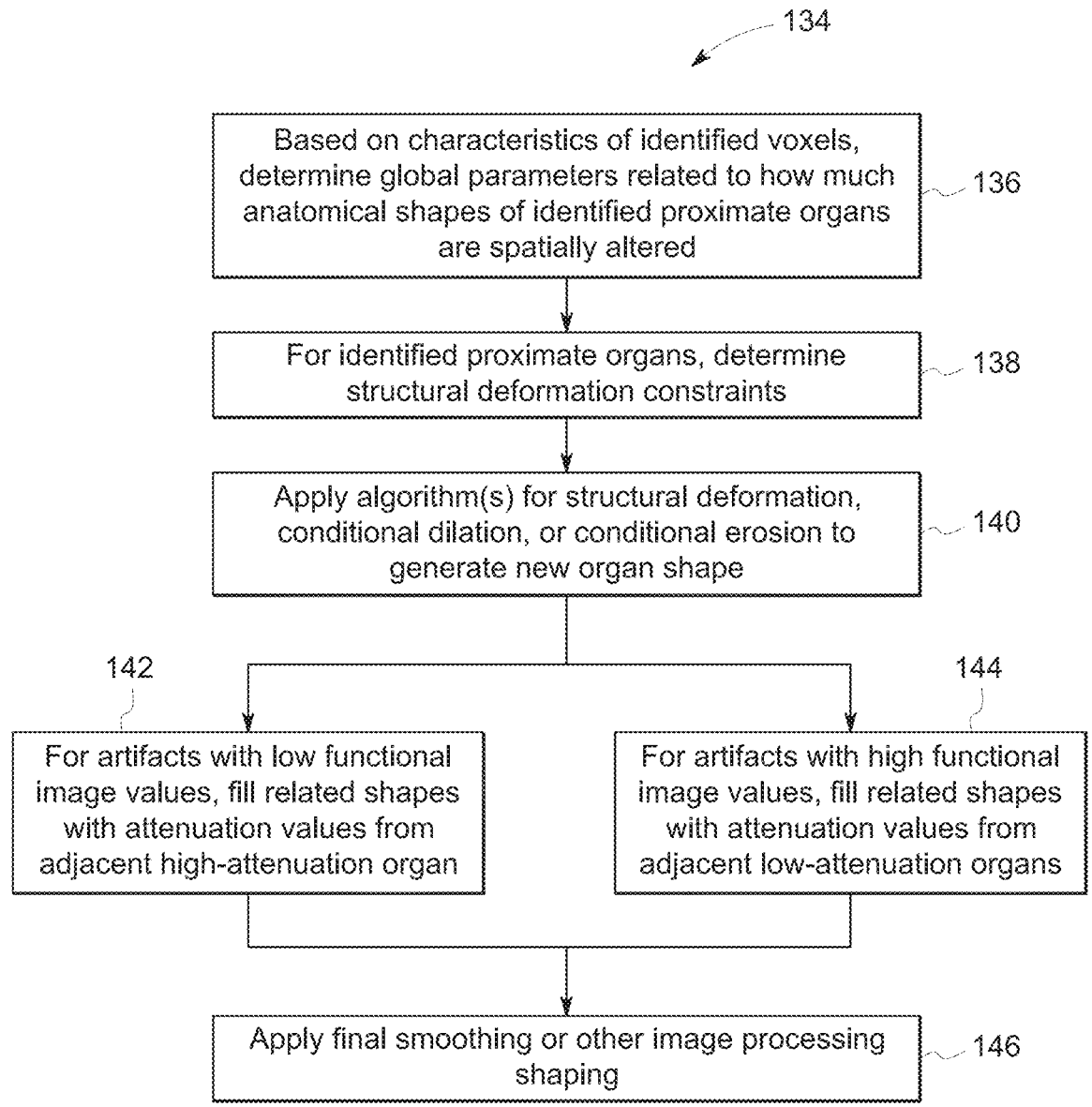
FIG. 6 is a flowchart of a method for correcting an anatomical image volume, in accordance with aspects of the present disclosure.

FIG. 6 is a flowchart of a method 134 for correcting an anatomical image volume (e.g., block 110 of the method 96 in FIG. 4). One or more steps of the method 134 may be performed by processing circuitry of the imaging systems discussed above or processing circuitry of a remote computing device having processing circuitry and memory circuitry. One or more of the steps of the method 134 may be performed simultaneously or in a different order from the order depicted in FIG. 6.

The method 134 includes determining, based on the characteristics of the identified voxels of the confirmed attenuation-correction image artifacts, global parameters related to how much anatomical shapes of the identified proximate organs are spatially altered to correct for the functional-anatomical spatial mismatch (block 136). Examples of spatial alteration include expansion, contraction, and/or translation. For example, for the diaphragm, the global parameters may include how much to move the diaphragm up or down (e.g., relative to center or another reference point). As another example, for the diaphragm, the global parameters may include how much to adjust the curvature.

The method 134 also includes determining, for the identified proximate organs, structural deformation constraints based on the pre-determined dedicated model (block 138). The constraints may be related to spatial limits, edge smoothness, shape continuation, and/or pre-determined morphology.

The method 134 further includes applying, based on the global parameters and the structural deformation constraints, one or more algorithms for structural deformation, conditional dilation, and/or conditional erosion to artificially generate a new organ shape in the corrected anatomical image volume (block 140). In certain embodiments, if there are artifacts in different organs, a respective new organ shape may be determined for the different organs with the artifacts.

In certain embodiments, subsequent to generating the new organ shape, the method 134 includes filling, for confirmed attenuation-correction image artifacts with the relatively low functional image values, filling respective new organ shapes with attenuation values from an adjacent high-attenuation organ (block 142). In certain embodiments, subsequent to generating the new organ shape, the method 134 includes filling, via the processor, for confirmed attenuation-correction image artifacts with the relatively high functional image values, filling the respective new organ shapes with attenuation values from an adjacent low-attenuation organ (block 144). In certain embodiments, the method 134 includes applying a final smoothing or image processing shaping if needed (block 146).

As an example for the application of the method 134, in the case of respiratory mismatch in the lower lung regions, the shape of the moving diaphragm along respiratory cycle is generally predictable, and it directly affects the deformation of the adjacent organs (e.g., located above and below). Therefore, the structural deformation constraints can be determined with only a few model parameters. In the case of mismatch caused by the cardiac cycle (e.g., in the heart region), the deformation along the cycle can be predicted as well. Returning to the diaphragm example, if the model parameters (e.g., derived from the artifact analysis step) indicate that the diaphragm should move upward 15 mm on its center and only 2 mm on its circumference, all of the soft tissues below the lungs will be expanded upward (and based on their CT HU) replacing CT lung tissue values, which results in imitating an exhale process. The amount of expansion in each XY location will be related to its position relative to the diaphragm center. Although such artificial deformation may not be anatomically accurate, it will give much better attenuation correction in the PET image reconstruction process, leading to new images without artifacts.

Figure 7:
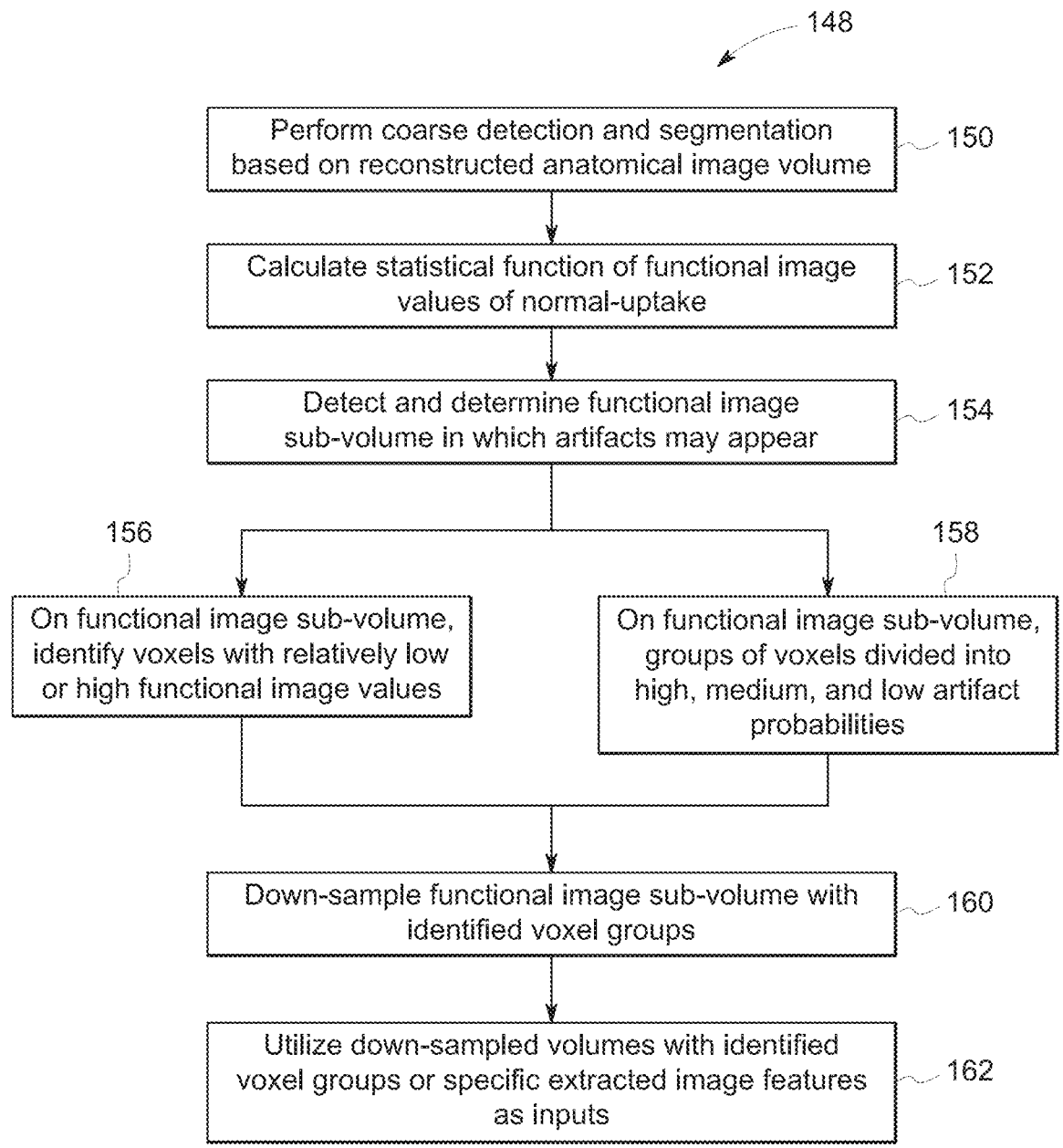
FIG. 7 is a flowchart of a method for detecting attenuation-correction image artifacts and estimating model parameters of the attenuation-correction image artifacts (e.g., utilizing machine-learning techniques or deep-learning techniques), in accordance with aspects of the present disclosure.

In certain embodiments, machine-learning techniques and deep-learning techniques (e.g., utilizing one or more trained neural networks) may be utilized for detecting/identifying attenuation-correction image artifacts and estimating model parameters of the attenuation-correction image artifacts (e.g., blocks 106 and 108 of the method 96 in FIG. 4). FIG. 7 is a flowchart of a method 148 for detecting attenuation-correction image artifacts and estimating model parameters of the attenuation-correction image artifacts (e.g., utilizing machine-learning techniques or deep-learning techniques). For the method 148, artifact evaluation in the diaphragm vicinity (i.e., the regions of the lower lungs and the upper liver and spleen) is utilized as an example. One or more steps of the method 148 may be performed by processing circuitry of the imaging systems discussed above or processing circuitry of a remote computing device having processing circuitry and memory circuitry. One or more of the steps of the method 148 may be performed simultaneously or in a different order from the order depicted in FIG. 7.

The method 148 includes preforming coarse detection and segmentation of the lungs, the liver, and the whole-patient soft tissues based on the corresponding reconstructed anatomical image volume (block 150). The method 148 also includes, with respect to the corresponding reconstructed anatomical image volume, calculating a statistical function of the functional image values of the normal-uptake for each segmented organ or group of tissues (block 152). In certain embodiments, the statistical function may be the median value distribution. In certain embodiments, a different percentile (or other criteria) other than the median can be pre-determined to be utilized to reflect the normal tracer uptake in the segmented organ or group of tissues.

The method 148 further includes, based on the segmented organs and/or tissue groups, detecting and determining the sub-volume in which image artifacts (e.g., attenuation-correction image artifacts) may appear and be considered (block 154). In certain embodiments, the method 148 even further includes, on the functional image sub-volume, identifying voxels with relatively low or relatively high functional image values comparted to the normal uptake values (obtained in block 152) based on pre-determined criteria (block 156). The pre-determined criteria may be a combination of relative ratios and thresholds. In certain embodiments, the method 148 includes generating or identifying, on the functional image sub-volume, groups of voxels divided into high, medium, and low artifact probabilities (e.g., with different discrete values (e.g., functional image values) for each group (block 158).

In certain embodiments, the method 148 includes downsampling the functional image sub-volume with the identified voxel groups to create a more efficient machine learning or deep-learning process that would require less training data (block 160). In certain embodiments, the method 148 utilizes the down-sampled volumes with the identified voxel groups or specific extracted image features (e.g., from the functional image sub-volume) as inputs to a machine-learning model or deep-learning model (e.g., having one or more trained neural networks) (block 162). As an example, the target for each input may be the required average expansion or contraction in mm up or down (corresponding to patient breathing and diaphragm motion model) and/or a mean diaphragm curvature parameter (overall two-scalar output).

In the method 148, the voxel group of suspected artifacts are automatically marked and scored (e.g., with a value within a pre-determined range) for each identified suspected voxel within a pre-determined sub-volume. The required few deformation model parameters may be directly calculated from the marked group of voxels using a complicated transform function that can be set and trained with various machine-learning techniques. For the training, a sufficiently large set of training data is required.

Figure 8:
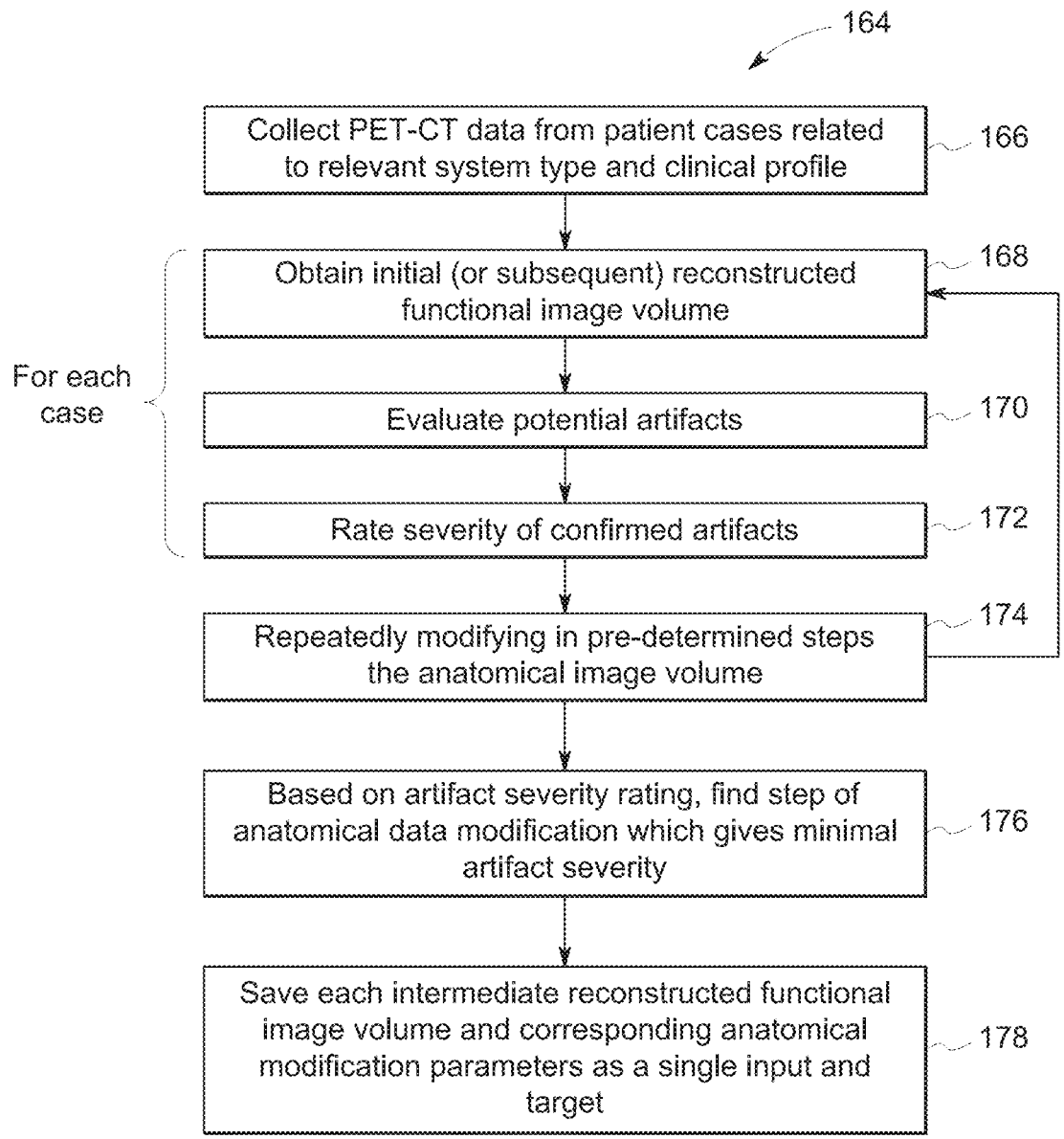
FIG. 8 is a flowchart of a method for generating training data for machine-learning- or deep-learning-based detection of attenuation-correction image artifacts and estimation of model parameters of the attenuation-correction image artifacts, in accordance with aspects of the present disclosure.

FIG. 8 is a flowchart of a method 164 for generating training data for machine-learning- or deep-learning-based detection of attenuation-correction image artifacts and estimation of model parameters of the attenuation-correction image artifacts (i.e., for training the machine-learning- or deep-learning model or algorithm utilized in the method 148 in FIG. 7). The method 164 is fully automatic and does not utilize any human-based image evaluation. One or more steps of the method 164 may be performed by processing circuitry of the imaging systems discussed above or processing circuitry of a remote computing device having processing circuitry and memory circuitry. One or more of the steps of the method 164 may be performed simultaneously or in a different order from the order depicted in FIG. 8.

The method 164 includes obtaining or collecting a large set of PET-CT case data from cases from a plurality of subjects related to a relevant system type (imaging system type) and a relevant clinical protocol (block 166). The method 164 also includes, for each case: obtaining an initial reconstructed functional image volume (or generating subsequent reconstructed functional image volume) (block 168), evaluating potential artifacts (e.g., attenuation-correction image artifacts) in the initial reconstructed functional image volume (block 170), and rating a severity of each identified or confirmed artifact (block 172). The method 164 further includes repeatedly modifying in pre-determined steps (of organ expansion or contraction) the reconstructed functional image volume based on the pre-determined dedicated model (block 174). In each modifying step, the method 164 includes reconstructing the modified functional image volume (block 168) and repeating blocks 170 and 172. The method 164 even further includes, based on the artifact severity rating, finding the step of the anatomical data modification which gives the minimal artifact severity (i.e., with least artifact severity) (block 176). The anatomical organ state of the step of the anatomical data modification with the minimal artifact severity is considered the optimal functional-anatomical matching. The method 164 still further includes saving, each intermediate reconstructed functional image volume and the corresponding recorded anatomical modification parameters (as determined relative to the found optimal state) as a single input and target to a machine-learning model or deep-learning model training scheme (block 178).

Figure 9:
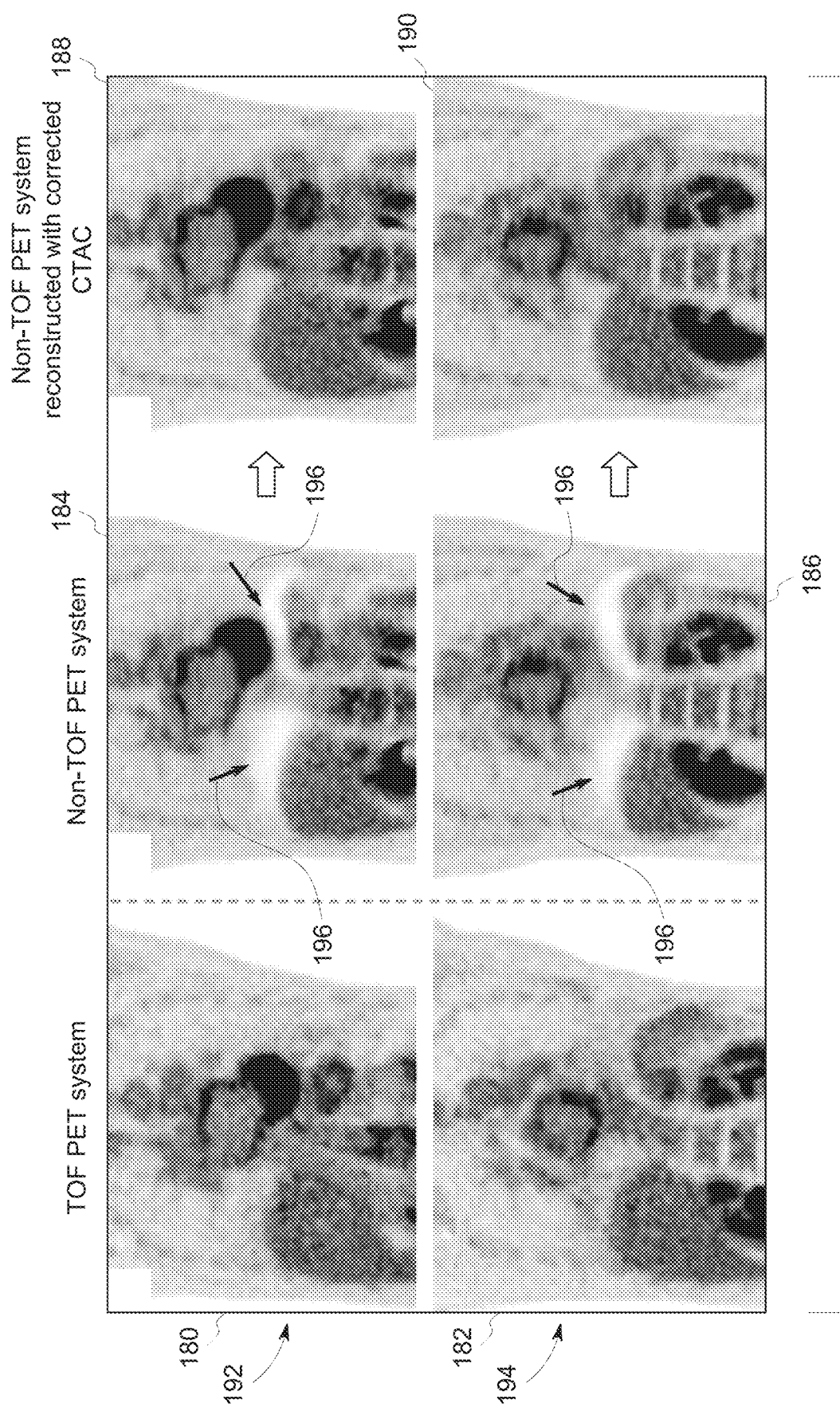
FIG. 9 provides examples of images of a patient illustrating results of automatic artifact evaluation and correction.

FIG. 9 provides examples of images of a patient illustrating results of automatic artifact evaluation and correction utilizing the techniques described above (e.g., the method 96 in FIG. 4). The images were obtained of the patient scanned consecutively on two different PET-CT systems (i.e., a TOF PET system and a non-TOF PET system). The non-TOF PET system is configured for a whole body scan. Images 180, 182 were obtained on the TOF PET system (i.e., a PET system with TOF reconstruction). Images 184, 186, 188, 190 were obtained on the non-TOF PET system (i.e., a PET system without TOF reconstruction). The images 180, 184, 188 in row 192 are of a first coronal position. The images 182, 186, 190 in row 194 are of a second different coronal position. The images 180, 182 from the TOF PET system lack attenuation-correction artifacts. The images 184, and 186 from the non-TOF PET system, when utilizing non-TOF PET reconstruction, include significant and severe attenuation-correction artifacts (e.g. due PET-CT respiratory mismatch) as indicated by the arrows 196. The algorithm disclosed in the method 96 in FIG. 4 was directly applied to the original PET and CT data and new reconstructed image volumes were generated (i.e. images 188, 190). The images are free of attenuation-correction artifacts.

Figure 10:
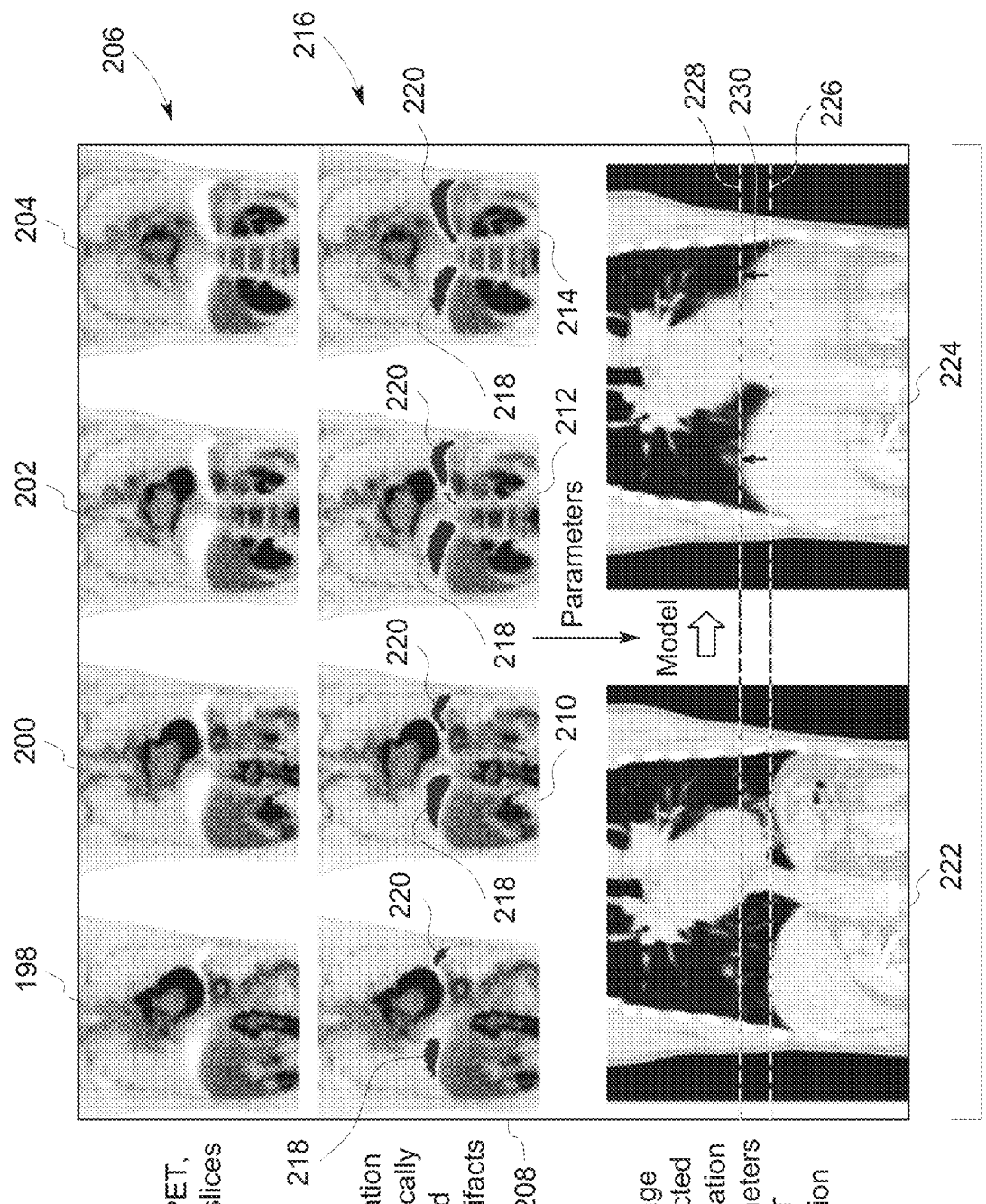
FIG. 10 provides examples of images of a patient illustrating application of automatic artifact evaluation and correction.

FIG. 10 provides examples of images of a patient illustrating application of automatic artifact evaluation and correction utilizing the techniques described above (e.g., the method 96 in FIG. 4). The images were obtained from a scan of a patient on a non-TOF PET system. Images 198, 200, 202, 204 in row 206 are the original PET reconstructed images for four different coronal slices. Attenuation-correction related image artifacts are evaluated and scored by a dedicated algorithm. The algorithm was applied to the whole image volume which includes images 198, 200, 202, 204. Images 208, 210, 212, 214 in row 216 illustrate highlighted regions 218, 220 detected as potential artifacts by the algorithm in the PET data. The evaluation of these artifacts results in the generation of key parameters for the CT deformation model. The model is specific for the lower lung regions and the adjacent organs. The CT deformation model creates an artificial CT image volume which is then used to reconstruct a corrected PET image volume (with more accurate attenuation correction). Image 222 is a coronal slice of the CTAC image volume acquired from the patient (i.e., original CTAC image volume) prior to correction with the deformation model and the model parameters from the PET artifact evaluation. Image 224 is a coronal slice of the corrected CTAC image volume (i.e., artificial image volume). Lines 226, 228 indicate the changes to the liver and spleen shapes on the CT image volume (e.g., the shift upward as indicated by the arrows 230). Lighter (e.g., white) artifacts (as seen in the images 198, 200, 202, 204) in the original PET data are typically corrected with a lift (e.g., shift up), while darker (e.g., black) artifacts are typically lowered (e.g., shifted down). The image-based algorithmic steps show in FIG. 10 (and described in the method 96 in FIG. 4) are fully 3D.

Technical effects of the disclosed embodiments include providing systems and methods for providing an approach that can be utilized in situations where severe artifacts exist and any spatial registration algorithms between the PET and CT images cannot provide the required result. In addition, the disclosed systems and methods provide an approach that is particularly suited for large axial coverage non-TOF PET systems (e.g., total body PET systems). The disclosed embodiments can be applied to correct similar artifacts in cardiac PET-CT and other multi-modalities (e.g., SPECT-CT and PET-MRI).

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer-implemented method for automatic artifact evaluation and correction in medical imaging data, comprising:
    obtaining, via a processor, emission-tomography functional image data and a corresponding reconstructed anatomical image volume of a subject, the emission-tomography functional image data and the corresponding reconstructed anatomical image volume comprising at least one organ having natural motion;
    pre-determining, via the processor, a dedicated model for spatial mismatch correction of the at least one organ having natural motion;
    performing, via the processor, initial image reconstruction of the emission-tomography functional image data to generate a reconstructed emission-tomography functional image volume utilizing attenuation correction based on the corresponding reconstructed anatomical image volume;
    identifying, via the processor, relevant anatomical regions, within the reconstructed emission-tomography functional image volume and the corresponding reconstructed anatomical image volume, where functional image quality may be affected by the natural motion of the at least one organ;
    identifying and evaluating, via the processor, potential attenuation-correction image artifacts in the reconstructed emission-tomography functional image volume that are related to functional-anatomical spatial mismatch;
    estimating, via the processor, model parameters based on confirmed attenuation-correction image artifacts, wherein the model parameters represent the functional-anatomical spatial mismatch;
    correcting, via the processor, the corresponding reconstructed anatomical image volume utilizing both the dedicated model and the model parameters to generate a corrected anatomical image volume; and
    reconstructing, via the processor, the emission-tomography functional image data utilizing attenuation correction based on the corrected anatomical image volume to generate a corrected emission-tomography functional image volume.

2. The computer-implemented method of claim 1, the method further comprising generating, via the processor, an attenuation map from the corrected anatomical image volume, wherein the attenuation map is utilized in reconstructing the emission-tomography functional image data to generate the corrected emission-tomography functional image volume.

3. The computer-implemented method of claim 1, wherein identifying and evaluating, via the processor, the potential attenuation-correction image artifacts comprises:
    identifying, for each identified relevant body region, proximate organs and specific sub-regions with the potential attenuation-correction image artifacts;
    calculating functional image values of normal-uptake regions in the identified proximate organs;
    on the reconstructed emission-tomography functional image volume, identifying voxels with relatively low functional image values or relatively high functional image values compared to the calculated functional image values of the normal-uptake regions based on pre-determined criteria;
    on the reconstructed emission-tomography functional image volume, calculating characteristics of any identified voxels with the relatively low functional image values or the relatively high functional image values relative to the identified proximate organs;
    determining which of the potential attenuation-correction image artifacts are confirmed attenuation-correction image artifacts based on characteristics of the identified voxels; and
    determining characteristics of the confirmed attenuation-correction image artifacts relevant for attenuation correction based on the pre-determined criteria.

4. The computer-implemented method of claim 3, wherein estimating the model parameters based on confirmed attenuation-correction image artifacts comprises determining the model parameters based on the characteristics.

5. The computer-implemented method of claim 3, wherein correcting the corresponding reconstructed anatomical image volume comprises:
    determining, based on the characteristics of the identified voxels of the confirmed attenuation-correction image artifacts, global parameters related to how much anatomical shapes of the identified proximate organs are spatially altered to correct for the functional-anatomical spatial mismatch;
    determining, for the identified proximate organs, structural deformation constraints based on the dedicated model; and
    applying, based on the global parameters and the structural deformation constraints, one or more algorithms for structural deformation, conditional dilation, or conditional erosion to artificially generate a new organ shape in the corrected anatomical image volume.

6. The computer-implemented method of claim 5, comprising, subsequent to generating the new organ shape:
    filling, via the processor, for confirmed attenuation-correction image artifacts with the relatively low functional image values, filling respective new organ shapes with attenuation values from an adjacent high-attenuation organ; and
    filling, via the processor, for confirmed attenuation-correction image artifacts with the relatively high functional image values, filling the respective new organ shapes with attenuation values from an adjacent low-attenuation organ.

7. The computer-implemented method of claim 1, wherein identifying and evaluating the potential attenuation-correction image artifacts comprises utilizing a trained deep neural network to identify and evaluate the potential attenuation-correction image artifacts.

8. The computer-implemented method of claim 1, comprising causing, via the processor, display of the corrected emission-tomography functional image volume on a display.

9. A system for automatic artifact evaluation and correction in medical imaging data, comprising:
a memory encoding processor-executable routines;
a processor configured to access the memory and to execute the processor-executable routines, wherein the routines, when executed by the processor, cause the processor to:
obtain emission-tomography functional image data and a corresponding reconstructed anatomical image volume of a subject, the emission-tomography functional image data and the corresponding reconstructed anatomical image volume comprising at least one organ having natural motion;
pre-determine a dedicated model for spatial mismatch correction of the at least one organ having natural motion;
perform initial image reconstruction of the emission-tomography functional image data to generate a reconstructed emission-tomography functional image volume utilizing attenuation correction based on the corresponding reconstructed anatomical image volume;
identify relevant anatomical regions, within the reconstructed emission-tomography functional image volume and the corresponding reconstructed anatomical image volume, where functional image quality may be affected by the natural motion of the at least one organ;
identify and evaluate potential attenuation-correction image artifacts in the reconstructed emission-tomography functional image volume that are related to functional-anatomical spatial mismatch;
estimate model parameters based on confirmed attenuation-correction image artifacts, wherein the model parameters represent the functional-anatomical spatial mismatch;
correct the corresponding reconstructed anatomical image volume utilizing both the dedicated model and the model parameters to generate a corrected anatomical image volume; and
reconstruct the emission-tomography functional image data utilizing attenuation correction based on the corrected anatomical image volume to generate a corrected emission-tomography functional image volume.

10. The system of claim 9, wherein the routines, when executed by the processor, cause the processor to generate an attenuation map from the corrected anatomical image volume, wherein the attenuation map is utilized in reconstructing the emission-tomography functional image data to generate the corrected emission-tomography functional image volume.

11. The system of claim 9, wherein the routines, when executed by the processor, cause the processor, when identifying and evaluating the potential attenuation-correction image artifacts, to:
identify, for each identified relevant body region, proximate organs and specific sub-regions with the potential attenuation-correction image artifacts;
calculate functional image values of normal-uptake regions in the identified proximate organs;
on the reconstructed emission-tomography functional image volume, identify voxels with relatively low functional image values or relatively high functional image values compared to the calculated functional image values of the normal-uptake regions based on pre-determined criteria;
on the reconstructed emission-tomography functional image volume, calculate characteristics of any identified voxels with the relatively low functional image values or the relatively high functional image values relative to the identified proximate organs;
determine which of the potential attenuation-correction image artifacts are confirmed attenuation-correction image artifacts based on the characteristics of the identified voxels; and
determine characteristics of the confirmed attenuation-correction image artifacts relevant for attenuation correction based on the pre-determined criteria.

12. The system of claim 11, wherein the routines, when executed by the processor, cause the processor, when estimating the model parameters based on confirmed attenuation-correction image artifacts, to determine the model parameters based on the characteristics.

13. The system of claim 11, wherein the routines, when executed by the processor, cause the processor, when correcting the corresponding reconstructed anatomical image volume, to:
determine, based on the characteristics of the identified voxels of the confirmed attenuation-correction image artifacts, global parameters related to how much anatomical shapes of the identified proximate organs are spatially altered to correct for the functional-anatomical spatial mismatch;
determine, for the identified proximate organs, structural deformation constraints based on the dedicated model; and
apply, based on the global parameters and the structural deformation constraints, one or more algorithms for structural deformation, conditional dilation, or conditional erosion to artificially generate a new organ shape in the corrected anatomical image volume.

14. The system of claim 13, wherein the routines, when executed by the processor, cause the processor to:
subsequent to generating the new organ shape:
fill for confirmed attenuation-correction image artifacts with the relatively low functional image values, filling respective new organ shapes with attenuation values from an adjacent high-attenuation organ; and
fill for confirmed attenuation-correction image artifacts with the relatively high functional image values, filling the respective new organ shapes with attenuation values from an adjacent low-attenuation organ.

15. A non-transitory computer-readable medium, the computer-readable medium comprising processor-executable code that when executed by a processor, causes the processor to:
obtain emission-tomography functional image data and a corresponding reconstructed anatomical image volume of a subject, the emission-tomography functional image data and the corresponding reconstructed anatomical image volume comprising at least one organ having natural motion;
pre-determine a dedicated model for spatial mismatch correction of the at least one organ having natural motion;
perform initial image reconstruction of the emission-tomography functional image data to generate a reconstructed emission-tomography functional image volume utilizing attenuation correction based on the corresponding reconstructed anatomical image volume;

identify relevant anatomical regions, within the reconstructed emission-tomography functional image volume and the corresponding reconstructed anatomical image volume, where functional image quality may be affected by the natural motion of the at least one organ;

identify and evaluate potential attenuation-correction image artifacts in the reconstructed emission-tomography functional image volume that are related to functional-anatomical spatial mismatch;

estimate model parameters based on confirmed attenuation-correction image artifacts, wherein the model parameters represent the functional-anatomical spatial mismatch;

correct the corresponding reconstructed anatomical image volume utilizing both the dedicated model and the model parameters to generate a corrected anatomical image volume; and reconstruct the emission-tomography functional image data utilizing attenuation correction based on the corrected anatomical image volume to generate a corrected emission-tomography functional image volume.

16. The non-transitory computer-readable medium of claim 15, wherein the processor-executable code, when executed by the processor, cause the processor to generate an attenuation map from the corrected anatomical image volume, wherein the attenuation map is utilized in reconstructing the emission-tomography functional image data to generate the corrected emission-tomography functional image volume.

17. The non-transitory computer-readable medium of claim 15, wherein the processor-executable code, when executed by the processor, cause the processor, when identifying and evaluating the potential attenuation-correction image artifacts, to:

identify, for each identified relevant body region, proximate organs and specific sub-regions with the potential attenuation-correction image artifacts;

calculate functional image values of normal-uptake regions in the identified proximate organs;

on the reconstructed emission-tomography functional image volume, identify voxels with relatively low functional image values or relatively high functional image values compared to the calculated functional image values of the normal-uptake regions based on pre-determined criteria;

on the reconstructed emission-tomography functional image volume, calculate characteristics of any identified voxels with the relatively low functional image values or the relatively high functional image values relative to the identified proximate organs;

determine which of the potential attenuation-correction image artifacts are confirmed attenuation-correction image artifacts based on the characteristics of the identified voxels; and determine characteristics of the confirmed attenuation-correction image artifacts relevant for attenuation correction based on the pre-determined criteria.

18. The non-transitory computer-readable medium of claim 17, wherein the processor-executable code, when executed by the processor, cause the processor, when estimating the model parameters based on confirmed attenuation-correction image artifacts, to determine the model parameters based on the characteristics.

19. The non-transitory computer-readable medium of claim 17, wherein the processor-executable code, when executed by the processor, cause the processor, when correcting the corresponding reconstructed anatomical image volume, to:

determine, based on the characteristics of the identified voxels of the confirmed attenuation-correction image artifacts, global parameters related to how much anatomical shapes of the identified proximate organs are spatially altered to correct for the functional-anatomical spatial mismatch;

determine, for the identified proximate organs, structural deformation constraints based on the dedicated model; and apply, based on the global parameters and the structural deformation constraints, one or more algorithms for structural deformation, conditional dilation, or conditional erosion to artificially generate a new organ shape in the corrected anatomical image volume.

20. The non-transitory computer-readable medium of claim 19, wherein the processor-executable code, when executed by the processor, cause the processor to:

subsequent to generating the new organ shape:

fill for confirmed attenuation-correction image artifacts with the relatively low functional image values, filling respective new organ shapes with attenuation values from an adjacent high-attenuation organ; and fill for confirmed attenuation-correction image artifacts with the relatively high functional image values, filling the respective new organ shapes with attenuation values from an adjacent low-attenuation organ.

* * * * *